United States Patent
Patel

(10) Patent No.: US 6,846,785 B2
(45) Date of Patent: Jan. 25, 2005

(54) LIQUID SOAP WITH VITAMIN BEADS AND METHOD FOR MAKING SAME

(75) Inventor: Jayesh A. Patel, Chandler, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/210,105

(22) Filed: Jul. 31, 2002

(65) Prior Publication Data

US 2004/0023820 A1 Feb. 5, 2004

(51) Int. Cl.⁷ .................................................. A61K 7/00
(52) U.S. Cl. ....................... 510/130; 510/159; 510/425; 510/426; 510/429; 510/476; 510/477; 510/490
(58) Field of Search ................................ 510/130, 159, 510/429, 425, 426, 476, 477, 490

(56) References Cited

U.S. PATENT DOCUMENTS

| | | |
|---|---|---|
| 4,992,476 A | 2/1991 | Geria |
| 4,992,477 A | 2/1991 | Geria |
| 5,629,006 A | 5/1997 | Hoang et al. |
| 5,681,801 A * | 10/1997 | Zocchi ......................... 510/125 |
| 5,990,233 A | 11/1999 | Barron et al. |
| 6,001,788 A | 12/1999 | Jaworski et al. |
| 6,090,772 A | 7/2000 | Kaiser et al. |
| 6,107,261 A | 8/2000 | Taylor et al. |
| 6,113,892 A | 9/2000 | Newell et al. |
| 6,162,780 A | 12/2000 | Partee et al. |
| 6,339,058 B1 * | 1/2002 | Toussaint et al. ........... 510/425 |
| 6,380,150 B1 * | 4/2002 | Toussaint et al. ........... 510/425 |
| 6,395,691 B1 * | 5/2002 | Tsaur .......................... 510/130 |
| 6,420,333 B1 * | 7/2002 | Hsu et al. .................... 510/441 |

OTHER PUBLICATIONS

"Carbopol® Aqua™ SF–1 Polymer," BFGoodrich Technical Data Sheet, TDS–294, Dec. 2000.

* cited by examiner

Primary Examiner—Necholus Ogden
(74) Attorney, Agent, or Firm—Snell & Wilmer LLP

(57) ABSTRACT

A liquid soap having vitamin-containing microcapsules including a base having an anionic surfactant and a chelating agent, a cross-linked acrylic polymer suspending agent, and multiple vitamin-containing microcapsules uniformly suspended in the liquid soap. The liquid soap is formulated at an elevated temperature which is maintained throughout the formulation process.

9 Claims, No Drawings

LIQUID SOAP WITH VITAMIN BEADS AND METHOD FOR MAKING SAME

FIELD OF INVENTION

The present invention generally relates to a liquid soap, and more particularly, to a liquid soap with vitamin beads or microcapsules and a method for making the same.

BACKGROUND OF THE INVENTION

Liquid soaps and liquid soaps with vitamins are known in the art. Additionally, liquid personal cleansing products, including liquid soaps containing suspended beads or microcapsules, are also known in the art. Liquid soaps typically have a viscous liquid rheology, with low yield point, resulting in a liquid that is flowable even under conditions of low shear. In contrast, liquid soaps containing suspended beads or microcapsules typically have a gel-like rheology, with a pronounced yield point. This gel-like rheology is often required to prevent settling or other physical instability in the products during production, shipping, or use. However, the gel-like rheology is not a preferred rheology for a liquid soap or liquid cleansing product because of problems of product dispensing and aesthetics often associated with gel rheologies. Accordingly, there is a need met by the instant invention, for a liquid soap, or liquid personal cleansing compositions, capable of suspending beads or microcapsules in a stable fashion while simultaneously possessing a viscous liquid, as opposed to a gel-like, rheology.

Most liquid soap products are packaged in bottles having a pump type dispenser to facilitate use of the product without creating messy spills. However, the gel-type rheological make-up of the products often causes clogging of the pump due to collection of thick glumps of dried gel-type soap located on the outer opening of the pump dispenser.

The addition of vitamins and vitamin-containing beads to liquid soaps is also known in the art. However, because vitamin-containing beads or microcapsules in such products are generally suspended with xanthan gum, the products often appear hazy and have a more gel-like consistency rather than a viscous liquid consistency.

Accordingly, there is a need for a liquid soap having beads or microcapsules containing vitamins in which the beads or microcapsules are uniformly suspended in a stable fashion in the product, regardless of the temperature or viscosity of the liquid soap base in which the beads or microcapsules are suspended, and which said liquid soap deposits vitamins on the skin of the user during washing.

SUMMARY OF THE INVENTION

In accordance with a preferred embodiment of the present invention, a liquid soap comprises a base having at least an anionic surfactant and a chelating agent, a plurality of microcapsules containing at least one vitamin, and a cross-linked acrylic polymer suspending agent, where the processing of the formulation of the liquid soap containing the microcapsules is performed at a temperature within a range of about 35 to 40 degrees C. A benefit of the composition is the deposition of vitamins to the skin surface while maintaining uniform suspension of the microcapsules at elevated temperatures and decreased breakage of the microcapsules at reduced temperatures. This composition has also been found to exhibit an appropriate amount of clarity with respect to its appearance and has been proven to be visually well accepted by consumers.

The base preferably comprises a primary moisturizer, such as water, for example, which is mixed with an anionic surfactant such as, for example, ammonium lauryl sulfate and sodium laureth sulfate, and a chelating agent which may include, for example, but is not limited to tetrasodium EDTA or phosphates.

The microcapsules preferably comprise a natural polysaccharide matrix and active ingredients such as, for example, tocopheryl acetate and retinyl palmitate while the suspending agent is preferably a cross-linked, alkali-swellable acrylic emulsion polymer. Prior to formulation, the majority of the polymer's carboxyl functionality is in the protonated form. However, after neutralization of the polymer by adding it to the other ingredients of the liquid soap, its molecules ionize and expand to provide suspending and thickening properties. The microcapsules suspended in the liquid base preferably have a size within a range of about 700 to 1200 microns and preferably contain at least one of Vitamin A palmitate or Vitamin E acetate.

In accordance with a further aspect of the present invention, other ingredients may also be included in the liquid soap of the present invention. These include, for example, one or more humectants, one or more preservatives, one or more antibacterial agents, one or more fragrances, one or more nonionic surfactants, one or more antioxidants, one or more amphoteric surfactants, one or more colorants, and one or more neutralizers.

The present invention is also directed to a method for processing a liquid soap which includes the steps of preparing a liquid base, heating the liquid base to a temperature of about 35 to 40 degrees C. to form a batch liquid, maintaining the batch liquid at a temperature within a range of about 35 to 40 degrees C. throughout the entire formulation process, adding and mixing a plurality of microcapsules into the batch liquid; and adding and mixing a cross-linked acrylic polymer into the batch liquid. The step of preparing a liquid base may include adding at least one anionic surfactant and a chelating agent to a diluent such as water, for example. The method for processing the liquid soap may also include the steps of adding one or more of a humectant, a preservative, an antibacterial, a fragrance, a nonionic surfactant, an antioxidant, an amphoteric surfactant, a colorant, and a neutralizer. A second amphoteric surfactant may be added near the end of the process after addition of the cross-linked acrylic polymer to add viscosity. The batch liquid is continually mixed throughout the method for processing the liquid soap. Mixing methods are known in the art. A preferred mixing method is slow sweep mixing at a speed of 10 to 40 revolutions per minute (rpm) with side scrapers. Slow mixing with side scrapers and maintaining correct manufacturing temperature between 35 to 40 degrees C. can be utilized for any volume batch size of 1 pound to 100,000 pounds.

DETAILED DESCRIPTION OF PREFERRED EXEMPLARY EMBODIMENTS

Preferred exemplary embodiments of the present invention will hereafter be described in conjunction with the description that follows. It will be understood that the detail provided herein is for illustration purposes only and that the subject invention is not so limited.

While the specific formulations of liquid soap within the present invention will be described in greater detail hereinbelow, in general, a liquid soap formulation in accordance with the present invention comprises a liquid soap base, a plurality of microcapsules containing at least one skin benefit agent, e.g., a vitamin, and a suspending agent for suspending the microcapsules in the liquid soap base. Preferably, the microcapsules and suspending agent are added to the liquid base soap while temperature is maintained at a range of about 35 to 40 degrees C. Formulation of the liquid soap of the present invention at such elevated temperatures resulted in a formulation process which eliminated the introduction of air into the liquid soap product thereby enabling the production of a continuously clear looking product without air bubbles. Once the clear liquid soap product was obtained, care was taken to transport the product to bottles without the introduction of air into the product.

Preferably, the liquid base soap comprises an inert diluent or primary moisturizer, at least one anionic surfactant, and a chelating agent. The inert diluent or primary moisturizer preferably comprises water in an amount from about 20 to about 40 weight %, and more preferably from about 25 to about 35 weight %. Preferably, the anionic surfactant is present in a total amount of about 1 to 40 weight % and more preferably comprises ammonium lauryl sulfate in an amount of about 5 to 20 weight %, preferably 12 weight %, and sodium laureth sulfate, such as standapol ES-2 manufactured by Cognis, Inc., in an amount of about 1 to 40 weight %, and preferably 5 to 20 weight %. Specific surfactants that can be used in the base include, but are not limited to, lauryl sulfates, octyl sulfates, 2-ethylhexyl sulfates, lauramine oxide, decyl sulfates, tridecyl sulfates, cocoates, lauryl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, cocamine oxide, decylamine oxide, myristamine oxide, ricinoleates, cetyl sulfates, and similar surfactants. Additional examples of surfactants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 10–13, 42–46, and 87–94, incorporated herein by reference. Suitable anionic surfactants include, but are not limited to, compounds in the classes known alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxylethelyne sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference.

The chelating agent is present in an amount of about 0.01 to 1.0 weight %, and more preferably about 0.02 to 0.05 weight %. Suitably, the chelating agent comprises tetrasodium EDTA or other EDTA salts.

The base liquid soap may include other additives such as humectants, preservatives, and vitamins. Humectants may comprise about 0.1 to 5 weight % of the base liquid while preservatives may comprise about 0.1 to 1.0 weight % of the base liquid. Suitable humectants include glycerin and any other humectants listed in the CTFA Handbook, which are herein incorporated by reference, and suitable preservatives include DMDM hydantoin and any other preservatives listed in the CTFA Handbook, which are also herein incorporated by reference. Vitamins, such as Vitamin E acetate and Vitamin A palmitate, for example, may be present in the base liquid soap in an amount of about 0.1 to 1.0 weight %, and preferably in an amount of about 0.01 to 0.5 weight %.

The liquid soap of the present invention may also include other conventional additives such as antibacterials, nonionic surfactants, antioxidants, amphoteric surfactants, neutralizers, colorants, and fragrances. The amounts of such additives will be dependent upon the desired liquid soap end product of the present invention. The final liquid soap product of the present invention may generally comprise antibacterials in an amount of about 0.1 to about 1.0 weight %, nonionic surfactants in an amount of about 1 to about 40 weight %, amphoteric surfactants in an amount of about 1 to 10 weight %, and neutralizers in an effective amount for neutralization of the acrylates polymer. Consumer acceptable amounts of dyes and fragrances may also be added in sufficient amounts to perform their intended function without adversely affecting the clarity and stability of the base liquid soap. All such additives are added to the base liquid soap while maintaining a product temperature between about 35 to 40 degrees C.

The liquid soap of the present invention also includes microcapsules or beads which contain at least one vitamin, such as Vitamin E and/or Vitamin A. The microcapsules preferably comprise a natural polysaccharide matrix such as, for example, agar/alginate/chitosan, which contains active ingredients such as tocopheryl acetate and retinyl palmitate. The tocopheryl acetate and the retinyl palmitate preferably comprise about 0.1 weight % and about 0.01 weight %, respectively, of the microcapsules. The microcapsules containing vitamins preferably have a size of about 700 to 1200 microns and are preferably contrasting color in order to maximize contrast with the base liquid soap. An example of one preferred bead includes a bead having mica to make the beads shiny and further enhance their visual effect. The microcapsule containing vitamins are preferably custom designed by a manufacturer such as Cognis Iberia S.L. located in Spain which can make the core of the microcapsules hard enough to withstand the surfactants contained in the liquid soap composition while also manipulating the internal phases of the microcapsules with mineral oil and glycolic acid in order to have the microcapsules achieve densities that are similar to the density of the liquid soap so that the microcapsules can be uniformly suspended in the liquid soap also suspended without settling or creaming.

The microcapsules are an essential part of the liquid soap product of the present invention in that they add both functionality and an attractive appearance to the liquid soap product. The microcapsules must have a hard external face to withstand the chemical action of the surfactant system contained within the liquid soap and must also withstand physical manipulation and mechanical breakage. The core and internal phase of the microcapsules must also be able to withstand harsh temperature changes because processing and transportation may expose the product to extremes of temperature.

The liquid soap of the present invention also includes a cross-linked acrylic polymer which functions as a suspending agent for the vitamin-containing microcapsules. The cross-linked acrylic polymer is preferably an alkali-swellable acrylic emulsion polymer having the majority of its carboxyl functionality in the protonated form. Prior to neutralization, the polymer molecules are coiled and impart relatively little suspension and viscosity. Once neutralized, the molecules ionize and expand due to the charge repulsion of the anionic carboxylate and thereby provide suspending and thickening properties. Preferably, the cross-linked acrylic polymer is present in an amount of about 5.75 to 7.00 weight % of the final liquid soap product of the present invention and preferably comprises Carbopol AQUA SF-1 polymer manufactured by BF Goodrich. Carbopol AQUA SF-1 which is approximately 70 weight % water and 30 weight % proprietary polymer/solids. It is recommended that Carbopol AQUA SF-1 be added to the free water of a formulation with gentle mixing at the start of the batching process. It is also recommended that amphoteric surfactants be added prior to neutralizing the Carbopol AQUA SF-1.

However, in contrast to the Carbopol AQUA SF-1 recommendations, the liquid soap of the present invention is formulated by adding diluted carbopol AQUA SF-1 near the end of the formulation process after adding surfactants. In addition, with the liquid soap of the present invention, an amphoteric surfactant may also be added after neutralizing the Carbopol AQUA SF-1.

In formulating the liquid soap of the present invention, the base liquid soap of the present invention is first formulated by adding at least one anionic surfactant and a chelating agent to an inert diluent, such as water, and heating the solution to a temperature of about 35 to 40 degrees C., and preferably about 36 to 37 degrees C. Other ingredients may also be added to the base liquid soap such as humectants and preservatives. Mixing of the base liquid soap should be maintained at about 10 to 40 revolutions per minute throughout the batch and the temperature should be maintained between 35 to 40 degrees C. throughout the batch. Once all ingredients are added to the base liquid soap, the batch should be mixed for approximately 5 minutes or until the mixture is clear.

Next, several additives may be incorporated into the mixture prior to the addition of the vitamin-containing microcapsules. Antibacterials, fragrance, nonionic surfactants, and antioxidants may each be added one at a time to the batch and mixed thoroughly between additions. After all are added, the batch is preferably mixed for about 15 minutes while the temperature continues to be maintained between about 35 to 40 degrees C. An amphoteric surfactant may then be added to the batch and mixed into the batch for approximately 10 minutes while continuing to maintain the temperature between about 35 to 40 degrees C.

Vitamin-containing microcapsules such as those described above are then added to the batch and mixed into the batch. The mixing speed is adjusted to adequately disperse the microcapsules into the batch while still maintaining the temperature between about 35 to 40 degrees C. One or more colorants are then added to the batch and mixed into the batch. The colorants may also be added to the batch prior to adding the vitamin-containing microcapsules.

The cross-linked acrylic polymer, such as Carbopol AQUA SF-1, is then premixed with an inert diluent, such as water, in a ratio of preferably about 3 to 1, or a little less, and is then slowly added to the batch while maintaining the temperature of the batch between about 35 to 40 degrees C. The batch is then mixed for at least 10 minutes after adding the diluted cross-linked acrylic polymer. A neutralizer, such as sodium hydroxide pellets predissolved in warm water, is then slowly added to the batch until the batch clears while maintaining the 35 to 40 degree C. temperature. Sodium hydroxide is added in an amount sufficient to achieve a preferable pH of about 6 to 7. To achieve clarity, the batch will require mixing the batch for about 10 to 15 minutes while maintaining the temperature of the batch. Finally, an amphoteric surfactant such as cocamidopropyl betaine and cocamide MEA manufactured under the trade name Mackman BC 39 by McIntyre, Inc., based in Chicago, in an amount of about 1 to 10 weight % of the final liquid soap product is added to the batch to add viscosity and is mixed until clear while maintaining the batch temperature. In one preferred method for making the liquid soap with vitamin beads of the present invention, the batch containing the final liquid soap product is mixed for about 15 minutes after obtaining a clear product.

A preferred final composition in accordance with the present invention includes the following components, all of which are listed in weight percent of the final product:

EXAMPLE 1

| Ingredient | Weight % |
| --- | --- |
| Purified water | 32.286 |
| Ammonium lauryl sulfate | 12.000 |
| Sodium laureth sulfate | 18.000 |
| Glycerin | 1.000 |
| Tetra sodium EDTA | 0.050 |
| DMDM hydantoin | 0.400 |
| DL Panthenol | 0.020 |
| Triclosan | 0.150 |
| Fragrance | 0.300 |
| Peg-18 glyceryl oleate/cocoate | 0.880 |
| Decyl polyglucose | 3.330 |
| Tocopheryl acetate | 0.200 |
| Cocamidopropyl betaine | 1.820 |
| Vitamin-containing microcapsules | 0.400 |
| 0.1% soln. of FD&C yellow No. 6 | 0.081 |
| 0.1% soln. of FD&C red No. 4 | 0.023 |
| Water | 17.000 |
| Acrylates copolymer | 6.200 |
| Water | 2.000 |
| Sodium hydroxide | 0.180 |
| Cocamidopropyl betaine and cocamide MEA | 3.680 |
| TOTAL | 100.000 |

It should be appreciated that the above formulation is set forth in an illustrative manner and that other liquid soap formulations having similar compositions and formulation steps are within the scope of the present invention. For example, other specific formulations which achieve near similar results with respect to clarity, uniform suspension of beads, vitamin deposition, and stability include:

EXAMPLE 2

| Ingredient | Weight % |
| --- | --- |
| Purified water | 32.736 |
| Ammonium lauryl sulfate | 12.000 |
| Sodium laureth sulfate | 18.000 |
| Glycerin | 1.000 |
| Tetra sodium EDTA | 0.050 |
| DMDM hydantoin | 0.400 |
| DL Panthenol | 0.020 |
| Triclosan | 0.150 |
| Fragrance | 0.300 |
| Peg-18 glyceryl oleate/cocoate | 0.880 |
| Decyl polyglucose | 3.330 |
| Tocopheryl acetate | 0.200 |
| Cocamidopropyl betaine | 1.820 |
| Vitamin-containing microcapsules | 0.400 |
| 0.1% soln. of FD&C yellow No. 6 | 0.081 |
| 0.1% soln. of FD&C red No. 4 | 0.023 |
| Water | 17.000 |
| Acrylates copolymer | 5.750 |

-continued

| Ingredient | Weight % |
| --- | --- |
| Water | 2.000 |
| Sodium hydroxide | 0.180 |
| Cocamidopropyl betaine and cocamide MEA | 3.680 |
| TOTAL | 100.000 |

EXAMPLE 3

| Ingredient | Weight % |
| --- | --- |
| Purified water | 32.486 |
| Ammonium lauryl sulfate | 12.000 |
| Sodium laureth sulfate | 18.000 |
| Glycerin | 1.000 |
| Tetra sodium EDTA | 0.050 |
| DMDM hydantoin | 0.400 |
| DL Panthenol | 0.020 |
| Triclosan | 0.150 |
| Fragrance | 0.300 |
| Peg-18 glyceryl oleate/cocoate | 0.880 |
| Decyl polyglucose | 3.330 |
| Tocopheryl acetate | 0.200 |
| Cocamidopropyl betaine | 1.820 |
| Vitamin-containing microcapsules | 0.400 |
| 0.1% soln. of FD&C yellow No. 6 | 0.081 |
| 0.1% soln. of FD&C red No. 4 | 0.023 |
| Water | 17.000 |
| Acrylates copolymer | 6.000 |
| Water | 2.000 |
| Sodium hydroxide | 0.180 |
| Cocamidopropyl betaine and cocamide MEA | 3.680 |
| TOTAL | 100.000 |

EXAMPLE 4

| Ingredient | Weight % |
| --- | --- |
| Purified water | 29.893 |
| Ammonium lauryl sulfate | 12.000 |
| Sodium laureth sulfate | 18.000 |
| Glycerin | 1.000 |
| Tetra sodium EDTA | 0.050 |
| DMDM hydantoin | 0.400 |
| DL Panthenol | 0.000 |
| Triclosan | 0.190 |
| Fragrance | 0.250 |
| Peg-18 glyceryl oleate/cocoate | 0.880 |
| Decyl polyglucose | 3.330 |
| Tocopheryl acetate | 0.250 |
| Cocamidopropyl betaine | 1.820 |
| Vitamin-containing microcapsules | 2.000 |
| FD&C yellow No. 6 | 0.00619 |
| FD&C red No. 4 | 0.00033 |
| Water | 17.000 |
| Acrylates copolymer | 7.000 |
| Water | 2.000 |
| Sodium hydroxide | 0.250 |
| Cocamidopropyl betaine and cocamide MEA | 3.680 |
| TOTAL | 100.000 |

The following materials were used as ingredients in the examples:

a) Alkyl polyglucoside (APG) manufactured by Henkel Co. in Hoboken, N.J. having the trade name PLANTAREN 2000 was used for the decyl polyglucose, b) Sodium Lauryl ether sulfate, 2 mole EO (SLES-2), manufactured by Henkel Corp. having the trade name STANDAPOL ES-2 was used as the sodium laureth sulfate, c) Triclosan (TCS), IRGASAN DP-300 manufactured by Ciba Specialty Chemical Corp. in Greensboro, N.C. was used for the triclosan, d) Glycerin (GLY) manufactured by Henkel/Emery in Cincinnati, Ohio was used for the glycerin, and e) Carbopol AQUA SF-1 polymer manufactured by B.F. Goodrich was used for the acrylates copolymer.

Examples of materials used for other listed ingredients can be found in U.S. Pat. No. 6,107,261 which is herein incorporated by reference in its entirety. The antibacterial composition described in U.S. Pat. No. 6,107,261 may comprise part of the base liquid soap of the present invention with some manipulation depending on the amounts of other ingredients listed above that are added to the liquid soap of the present invention.

Typically, most oils such as Vitamin E Acetate and Vitamin A Palmitate will wash off in surfactant based products. However, the formulation of the liquid soap of the present invention includes the steps of premixing nonionic surfactants into the batch liquid before adding the microcapsules containing the Vitamin E Acetate and/or Vitamin A Palmitate. This allows the Vitamin E Acetate and/or Vitamin A Palmitate to solubilize, aiding deposition of the vitamins on the skin of the user, and also prevents the product from becoming hazy in appearance.

The liquid soap of the present invention has many advantages. The liquid soap product of the present invention comprises a clear base with contrasting uniformly suspended vitamin-containing capsules. The liquid soap of the present invention contains a minimum number of air bubbles which completely disperse over time thereby enhancing the clarity of the product. The liquid soap of the present invention also enables deposition of vitamins contained in the formula to the skin surface.

Formulating the liquid soap of the present invention at a temperature of about 35 to 40 degrees C. both reduced air entrapment, thereby avoiding air bubbles, and increased the clarity of the product. The suspending agent used in the liquid soap of the present invention enables uniform suspension of the microcapsules regardless of the temperature and viscosity of the base liquid soap containing surfactants and is also effective in helping to produce a clear product. The liquid soap of the present invention has a liquid rheology, unlike the gelled rheology of other bead containing soaps, and preferably has a viscosity of about 5000 to 15000 centipoise using a Brookfield viscometer model LVF spindle #3 at 12 rpm and at 25 degrees C. The viscous liquid of the present invention, unlike gels, achieves a low yield stress.

The above described examples were tested for stability at one, two, three, four, eight and twelve weeks post production and were found to exhibit stable and acceptable pH and viscosity values. Freeze-thaw stability results of the product were also favorable.

It will be understood that the foregoing description is of preferred exemplary embodiments of the present invention, and that the present invention is not limited to the specific examples and compositions set forth herein. Such examples and compositions are for illustrative purposes only. Various modifications may be made in light thereof as will be suggested to persons skilled in the art without departing from the scope of the invention as expressed in the appended claims.

What is claimed is:

1. A liquid soap comprising:
   about 65 to about 75 weight % of a liquid base;
   about 0.1 to about 2.1 weight % of microcapsules; and
   about 20 to about 25 weight % of a suspending agent comprising a cross-linked acrylic polymer and water;
   wherein during formulation the liquid base is maintained at a temperature between about 35 to 40 degrees C. during addition of all other ingredients including the microcapsules and the suspending agent.

2. The liquid soap of claim 1 wherein the liquid base comprises an anionic surfactant and a chelating agent.

3. The liquid soap of claim 2 wherein the liquid base further comprises at least one of a humectant, a preservative, and a vitamin.

4. The liquid soap of claim 1 further comprising at least one of an antibacterial, a fragrance, a nonionic surfactant, an antioxidant, an amphoteric surfactant, a colorant, and a neutralizer.

5. The liquid soap of claim 1 wherein the microcapsules contain at least one of Vitamin A and Vitamin E.

6. The liquid soap of claim 1 wherein said microcapsules have a size within a range of about 700 to 1200 microns.

7. The liquid soap of claim 1 wherein the suspending agent comprises an alkali-swellable acrylic emulsion polymer.

8. The liquid soap of claim 3 wherein the liquid base comprises:
   about 20 to 40 weight % of a diluent;
   about 1 to 40 weight % of an anionic surfactant;
   about 0.1 to 5 weight % of a humectant;
   about 0.01 to 1.0 weight % of a chelating agent;
   about 0.1 to 1.0 weight % of a preservative; and
   about 0.1 to 1.0 weight % of a vitamin.

9. The liquid soap of claim 4 wherein said amphoteric surfactant comprises about 1.0 to 10.0 weight % of said liquid soap.

* * * * *